United States Patent [19]
Angell et al.

[11] Patent Number: 5,756,739
[45] Date of Patent: May 26, 1998

[54] PROCESS FOR PREPARING POLYAMINE DERIVATIVE AND INTERMEDIATES THEREOF

[75] Inventors: Paul T. Angell, Middletown; John Martin, Loveland, both of Ohio; Peter B. Anzeveno, Zionsville, Ind.

[73] Assignee: Merrell Pharmaceuticals Inc., Cincinnati, Ohio

[21] Appl. No.: 818,059

[22] Filed: Mar. 14, 1997

Related U.S. Application Data

[63] Continuation of Ser. No. 508,097, Jul. 27, 1995, which is a continuation of Ser. No. 358,053, Dec. 16, 1994, abandoned, which is a continuation of Ser. No. 133,484, Oct. 7, 1993, abandoned.

[51] Int. Cl.$^6$ .................................................. C07D 403/02
[52] U.S. Cl. .......................................... 544/296; 544/335
[58] Field of Search ................................. 544/296, 335

[56] References Cited

U.S. PATENT DOCUMENTS

| | | | |
|---|---|---|---|
| 5,091,576 | 2/1992 | Bergeron | 564/367 |
| 5,109,024 | 4/1992 | Prakash et al. | 514/674 |

FOREIGN PATENT DOCUMENTS

| | | |
|---|---|---|
| 0311068 | 4/1989 | European Pat. Off. |
| 0349224 | 6/1989 | European Pat. Off. |
| 0349224 | 1/1990 | European Pat. Off. |
| 94/07480 | 9/1993 | WIPO |

OTHER PUBLICATIONS

J. Med. Chem., 34, 2414–2420, 1991.
J. Med. Chem., 33, 1369–1375, 1990.
J. Org. Chem., 51, 5338–5341, 1986.
J. Org. Chem., 51, 4856–4861, 1986.
Nagarajan, et al., J. Org. Chem. 51:4856–4861 (1986).
Weiberth, et al., J. Org. Chem. 51:5338–5341 (1986).
Edwards, et al., Tetrahedron Letters 31(24):3417–3420 (1990).
Edwards, et al., J. of Med. Chem. 33:1369–1375 (1990).
Edwards, et al., J. of Med. Chem. 34:2414–2420 (1991).
Terry L. Bowlin, et al., Cancer Research (51) 62–66, 1991.
Terry L. Bowlin, et al., "Participation of T–Lymphocytes in the Curative Effect of a Novel Synthetic Polyamine Analogue, N,N'–Bis[3–(ethylamine)propyl]–1,7–heptanediamine, against L1210 Leukemia in Vivo", Cancer Research (51) 62–66, 1991.
Ganem, Acc. Chem. Res. 15:290–298 (1982).

*Primary Examiner*—Yogendra N. Gupta
*Attorney, Agent, or Firm*—David M. Stemerick

[57] ABSTRACT

The present invention provides a novel process for preparing polyamine derivatives and pharmaceutically acceptable salts thereof, which are useful as antineoplastic agents and to novel intermediates thereof.

9 Claims, No Drawings

PROCESS FOR PREPARING POLYAMINE DERIVATIVE AND INTERMEDIATES THEREOF

This is a continuation of application Ser. No. 08/508,097, filed Jul. 27, 1995, which is a continuation of Ser. No. 08/358,053, filed Dec. 16, 1994, now abandoned, which is a continuation of Ser. No. 08/133,484, filed Oct. 7, 1993, now abandoned, which is herein incorporated by reference.

The present invention relates to a novel process for preparing polyamine derivatives and pharmaceutically acceptable salts thereof, which are useful as antineoplastic agents [European Patent Application 0 311 068, Publication Date Mar. 4, 1989] and to novel intermediates thereof.

The process and intermediates of the present invention provide a novel method for preparing antineoplastic polyamine derivatives.

SUMMARY OF THE INVENTION

The present invention provides a novel process for preparing a compound of the formula

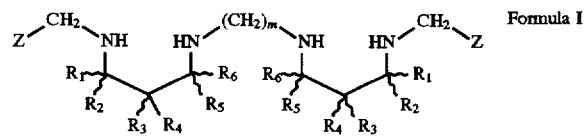
Formula I wherein m is 6, 7, 8, or 9, $R_1$, $R_2$, $R_3$, $R_4$, $R_5$, and $R_6$, are each independently hydrogen or a $C_1$–$C_3$ alkyl group with the proviso that the total number of carbon atoms incorporated by all the groups $R_1$, $R_2$, $R_3$, $R_4$, $R_5$, or $R_6$ may not exceed 6, Z is hydrogen, methyl, or ethyl;

and pharmaceutically acceptable salts thereof comprising the steps of:

(a) reacting a compound of the formula

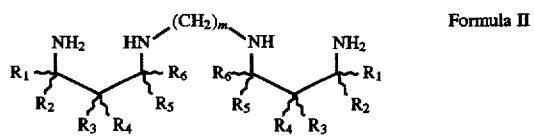
Formula II wherein m is 6, 7, 8, or 9, $R_1$, $R_2$, $R_3$, $R_4$, $R_5$, and $R_6$, are each independently hydrogen or a $C_1$–$C_3$ alkyl group with the proviso that the total number of carbon atoms incorporated by all the groups $R_1$, $R_2$, $R_3$, $R_4$, $R_5$, or $R_6$ may not exceed 6;

with an appropriate aldehyde to give a bis-hexahydropyrimidine derivative;

(b) reacting the bis-hexahydropyrimidine derivative with an appropriate acylating agent to give a bis-acylhexahydropyrimidine derivative;

(c) reacting the bis-acylhexahydropyrimidine derivative with an appropriate reducing agent to give a bis-alkylhexahydropyrimidine derivative;

(d) reacting the bis-alkylhexahydropyrimidine derivative with an appropriate solvolysis agent.

In addition, the present invention provides for novel bis-acylhexahydropyrimidine derivatives of the formula:

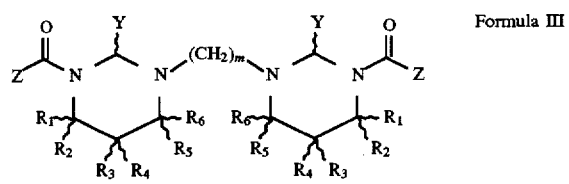
Formula III wherein m is 6, 7, 8, or 9, $R_1$, $R_2$, $R_3$, $R_4$, $R_5$, and $R_6$, are each independently hydrogen or a $C_1$–$C_3$ alkyl group with the proviso that the total number of carbon atoms incorporated by all the groups $R_1$, $R_2$, $R_3$, $R_4$, $R_5$, or $R_6$ may not exceed 6, Z is hydrogen, methyl, or ethyl, Y is hydrogen, $C_1$–$C_6$ alkyl, phenyl, or substituted phenyl In addition, the present invention provides for novel bis-alkylhexahydropyrimidine derivatives of the formula:

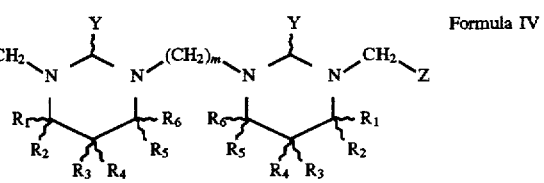
Formula IV wherein m is 6, 7, 8, or 9, $R_1$, $R_2$, $R_3$, $R_4$, $R_5$, and $R_6$, are each independently hydrogen or a $C_1$–$C_3$ alkyl group with the proviso that the total number of carbon atoms incorporated by all the groups $R_1$, $R_2$, $R_3$, $R_4$, $R_5$, or R6 may not exceed 6, Z is hydrogen, methyl, or ethyl, Y is hydrogen, $C_1$–$C_6$ alkyl, phenyl, or substituted phenyl.

DETAILED DESCRIPTION OF THE INVENTION

As used in this application:

a) the designation "⁓" refers to a bond for which the stereochemistry is not designated.

b) the term "pharmaceutically acceptable salts" refers to acid addition salts;

c) the term "$C_1$–$C_3$ alkyl" refers to a branched or straight chained alkyl radical containing from 1–3 carbon atoms, such as methyl, ethyl, n-propyl, and isopropyl;

d) the term "$C_1$–C6 alkyl" refers to a branched or straight chained, or cyclic alkyl radical containing from 1–6 carbon atoms, such as methyl, ethyl, n-propyl, isopropyl, n-butyl, isobutyl, t-butyl, n-pentyl, cyclopentyl, n-hexyl, cyclohexyl, and the like;

e) the term "phenyl" refers to;

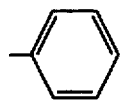

f) the term "substituted phenyl" refers to;

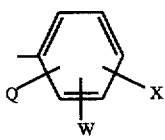

wherein

Q, W, and X are independently chosen from the group consisting of; hydrogen, $C_1$–$C_4$ alkyl, $C_1$–$C_4$ alkoxy, or halogen.

The expression "pharmaceutically acceptable acid addition salts" is intended to apply to any non-toxic organic or inorganic acid addition salt of the polyamine derivatives or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, and sulfonic acids such as p-toluenesulfonic acid, methane sulfonic acid and 2-hydroxyethane sulfonic acid. Such salts can exist in either a hydrated or substantially anhydrous form.

In compounds of the Formulas I, II, III, and IV there are two each of the groups $R_1$, $R_2$, $R_3$, $R_4$, $R_5$, and $R_6$. In compounds of the Formulas I, II, III, and IV in which one or more of the groups $R_1$, $R_2$, $R_3$, $R_4$, $R_5$, and R6 is other than hydrogen; the total number of carbons incorporated by all the groups $R_1$, $R_2$, $R_3$, $R_4$, R5, or $R_6$ may not exceed 6. Illustrative examples of compounds of Formula I which can be prepared by the present process containing groups $R_1$, $R_2$, $R_3$, $R_4$, $R_5$, and $R_6$ is other than hydrogen are;

$ZCH_2NHCH(CH_3)CH_2CH_2NH(CH_2)_mNHCH_2CH_2(CH_3)CHNHCH_2Z$, $ZCH_2NHCH(CH_2CH_3)CH_2CH_2NH(CH_2)_mNHCH2CH2(CH_2CH_3)CHNHCH_2Z$, $ZCH_2NHCH(CH_2CH_2CH_3)CH_2CH_2NH(CH_2)_mNHCH2CH_2(CH_2CH_2CH_3)CHNHCH_2Z$, $ZCH_2NHCH_2CH_2CH(CH_3)NH(CH2)_mNH(CH_3)CHCH_2CH_2NHCH_2Z$, $ZCH_2NHC(CH_3)_2CH_2CH_2NH(CH_2)_mNHCH_2CH_2(CH_3)_2CNHCH_2Z$, $ZCH_2NHCH_2CH(CH_3)CH_2NH(CH_2)_mNHCH_2(CH_3)CHCH_2NHCH_2Z$

These illustrative examples are not intended to limit the present invention in any way.

As is appreciated by one of ordinary skill in the art the compounds of the Formulas I, II, III, and IV in which one or more of the groups $R_1$, $R_2$, $R_3$, $R_4$, $R_5$, and $R_6$ are not hydrogen may exist as stereoisomers depending on the nature of $R_1$, $R_2$, $R_3$, $R_4$, $R_5$, and R6. In addition, the compounds of the Formulas II, III, and IV may exist as stereoisomers depending on the nature of $R_1$, $R_2$, $R_3$, $R_4$, $R_5$, $R_6$, and Y. Any reference in this application to one of the compounds of the Formulas I, II, III, and IV is meant to encompass either specific stereoisomers or a mixture of stereoisomers. The Cahn-Ingold-Prelog designation of (R)- and (S)- for the stereochemistry of compounds represented by Formula I, II, III, and IV depends on the nature of $R_1$, $R_2$, $R_3$, $R_4$, $R_5$, $R_6$, and Y. The specific stereoisomers can be prepared by stereospecific synthesis or can be separated and recovered by techniques known in the art, such as chromatography on chiral stationary phases, amide formation with a chiral acid followed by separation of the resultant diastereomeric amides and hydrolysis to the desired stereoisomer, or fractional recrystallization of addition salts formed by reagents used for that purpose, as described in "Enantiomers, Racemates, and Resolutions", J. Jacques, A. Collet, and S. H. Wilen, Wiley (1981).

Examples of compounds encompassed by the present invention include:

1,7-Bis-(3-acetylhexahydropyrimidin-1-yl)-heptane;
1,7-Bis-(3-formylhexahydropyrimidin-1-yl)-heptane;
1,7-Bis-(3-propionylhexahydropyrimidin-1-yl)-heptane;
1,6-Bis-(3-acetylhexahydropyrimidin-1-yl)-hexane;
1,6-Bis-(3-formylhexahydropyrimidin-1-yl)-hexane;
1,6-Bis-(3-propionylhexahydropyrimidin-1-yl)-hexane;
1,8-Bis-(3-acetylhexahydropyrimidin-1-yl)-octane;
1,8-Bis-(3-formylhexahydropyrimidin-1-yl)-octane;
1,8-Bis-(3-propionylhexahydropyrimidin-1-yl)-octane;
1,9-Bis-(3-acetylhexahydropyrimidin-1-yl)-nonane;
1,9-Bis-(3-formylhexahydropyrimidin-1-yl)-nonane;
1,9-Bis-(3-propionylhexahydropyrimidin-1-yl)-nonane;
(R, R)-1,7-Bis-(3-acetyl-4-methyl-hexahydropyrimidin-1-yl)-heptane;
(R, R)-1,7-Bis-(3-formyl-4-methyl-hexahydropyrimidin-1-yl)-heptane;
(R, S)-1,7-Bis-(3-formyl-4-methyl-hexahydropyrimidin-1-yl)-heptane;
(R, R)-1,7-Bis-(3-propionyl-4-methyl-hexahydropyrimidin-1-yl)-heptane;
(S, S)-1,7-Bis-(3-acetyl-4-methyl-hexahydropyrimidin-1-yl)-heptane;
(S, S)-1,7-Bis-(3-formyl-4-methyl-hexahydropyrimidin-1-yl)-heptane;
(S, S)-1,7-Bis-(3-propionyl-4-methyl-hexahydropyrimidin-1-yl)-heptane;
1,7-Bis-(3-ethylhexahydropyrimidin-1-yl)-heptane;
1,7-Bis-(3-methylhexahydropyrimidin-1-yl)-heptane;
1,7-Bis-(3-propylhexahydropyrimidin-1-yl)-heptane;
1,6-Bis-(3-ethylhexahydropyrimidin-1-yl)-hexane;
1,6-Bis-(3-methylhexahydropyrimidin-1-yl)-hexane;
1,6-Bis-(3-propylhexahydropyrimidin-1-yl)-hexane;
1,8-Bis-(3-ethylhexahydropyrimidin-1-yl)-octane;
1,8-Bis-(3-methylhexahydropyrimidin-1-yl)-octane;
1,8-Bis-(3-propylhexahydropyrimidin-1-yl)-octane;
1,9-Bis-(3-ethylhexahydropyrimidin-1-yl)-nonane;
1,9-Bis-(3-methylhexahydropyrimidin-1-yl)-nonane;
1,9-Bis-(3-propylhexahydropyrimidin-1-yl)-nonane;
(R, R)-1,7-Bis-(3-ethyl-4-methyl-hexahydropyrimidin-1-yl)-heptane;
(R, R)-1,7-Bis-(3-methyl-4-methyl-hexahydropyrimidin-1-yl)-heptane;
(R, S)-1,7-Bis-(3-methyl-4-methyl-hexahydropyrimidin-1-yl)-heptane;
(R, R)-1,7-Bis-(3-propyl-4-methyl-hexahydropyrimidin-1-yl)-heptane;
(S, S)-1,7-Bis-(3-ethyl-4-methyl-hexahydropyrimidin-1-yl)-heptane;
(S, S)-1,7-Bis-(3-methyl-4-methyl-hexahydropyrimidin-1-yl)-heptane;
(S, S)-1,7-Bis-(3-propyl-4-methyl-hexahydropyrimidin-1-yl)-heptane;
1,7-Bis-[(3-ethylamino)propyl]-heptanediamine;
1,7-Bis-[(3-methylamino)propyl]-heptanediamine;
1,7-Bis-[(3-propylamino)propyl]-heptanediamine;
1,6-Bis-[(3-ethylamino)propyl]-hexanediamine;
1,6-Bis-[(3-methylamino)propyl]-hexanediamine;
1,6-Bis-[(3-propylamino)propyl]-hexanediamine;

1,8-Bis-[(3-ethylamino)propyl]-octanediamine;
1,8-Bis-[(3-methylamino)propyl]-octanediamine;
1,8-Bis-[(3-propylamino)propyl]-octanediamine;
1,9-Bis-[(3-ethylamino)propyl]-nonanediamine;
1,9-Bis-[(3-methylamino)propyl]-nonanediamine;
1,9-Bis-[(3-propylamino)propyl]-nonanediamine;
(R, R)-1,7-Bis-[(3-ethylamino)-3-methyl-propyl]-heptanediamine;
(R, R)-1,7-Bis-[(3-methylamino)-3-methyl-propyl]-heptanediamine;
(R, S)-1,7-Bis-[(3-methylamino)-3-methyl-propyl]-heptanediamine;
(R, R)-1,7-Bis-[(3-propylamino)-3-methyl-propyl]-heptanediamine;
(S, S)-1,7-Bis-[(3-ethylamino)-3-methyl-propyl]-heptanediamine;
(S, S)-1,7-Bis-[(3-methylamino)-3-methyl-propyl]-heptanediamine;
(S, S)-1,7-Bis-[(3-propylamino)-3-methyl-propyl]-heptanediamine.

A general synthetic procedure for preparing polyamine derivatives, bis-acylhexahydropyrimidine derivatives, and bis-alkylhexahydropyrimidine derivatives is set forth in Scheme A. In Scheme A, all substituents unless otherwise indicated, are as previously defined. Starting materials, reagents, techniques, and procedures used in Scheme A are well known and appreciated by one of ordinary skill in the art.

SCHEME A

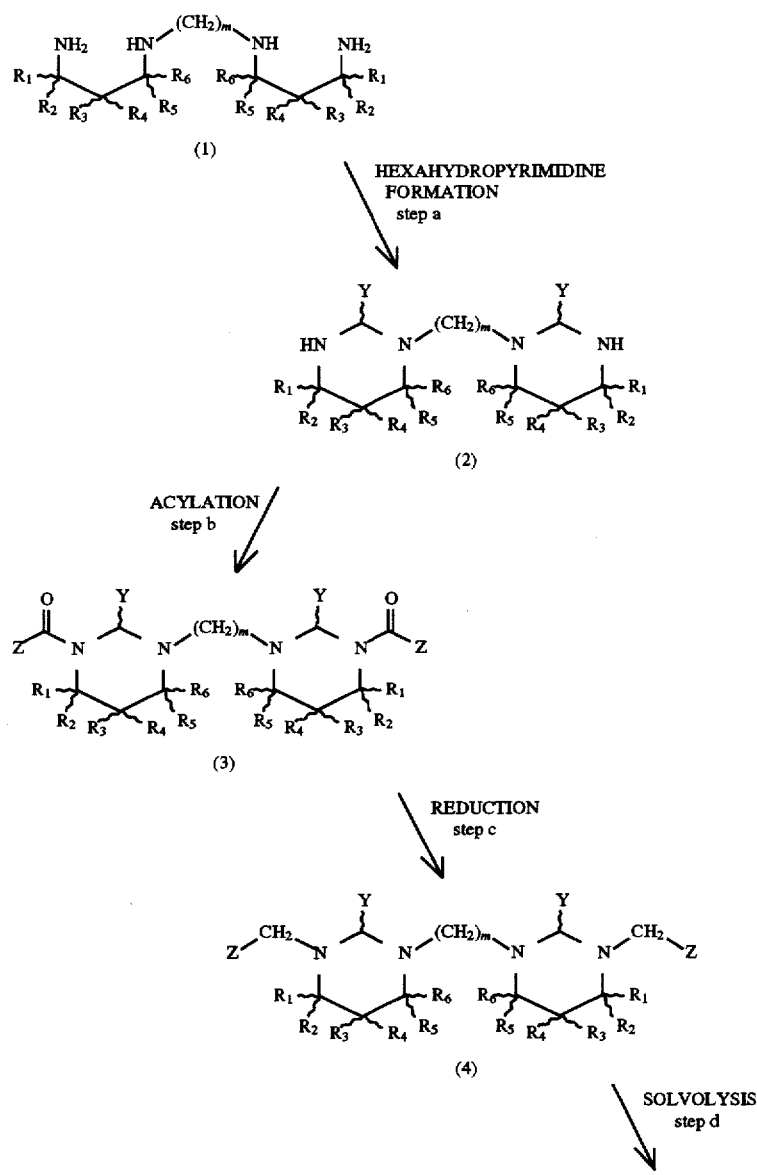

-continued
SCHEME A

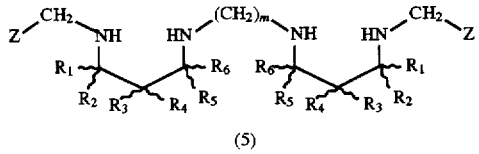

(5)

The compounds of structure (1) in which m and $R_1$, $R_2$, $R_3$, $R_4$, $R_5$, and $R_6$ are as defined above can be obtained by methods known in the art. Specifically, compounds of structure (1) in which m is 6,7,8, and 9; and $R_1$, $R_2$, $R_3$, $R_4$, $R_5$, and $R_6$ are hydrogen can be obtained by the methods in Prakash et al, U.S. Pat. No. 5,109,024, M. L Edwards et al, *J. Med. Chem.* 34, 2414–2420 (1991), and M. L Edwards et al, *J. Med. Chem.* 33, 1369–1375 (1990). The compounds of structure (1) in which m is 6,7,8, and 9; and $R_1$, $R_2$, $R_3$, $R_4$, $R_5$, and $R_6$ are independently $C_1$–$C_3$ alkyl can be obtained by methods known in the art or by methods known analogously in the art in Prakash et al, U.S. Pat. No. 5,109,024, M. L Edwards et al, *J. Med. Chem.* 34, 2414–2420 (1991), M. L Edwards et al, *J. Med. Chem.* 33, 1369–1375 (1990), M. L Edwards et al, *Tet, Lets.* 31, 3417–3420 (1990), F. J. Weiberth and S. S. Hall, *J. Org. Chem.*51, 5338–5341 (1986), and S. Nagarajan and B. Ganem, *J. Org. Chem.*51, 4856–4861 (1986).

In step a, a compound of structure (1) is is contacted with an appropriate aldehyde to form a bis-hexahydropyrimidine of structure (2).

For example, a compound of structure (1) or a salt of a polyamine of structure (1) is contacted with an appropriate aldehyde. Appropriate aldehydes are well known in the art and include but are not limited to benzaldehyde and form-aldehyde and formaldehyde equivalents, such as paraformaldehyde, dimethoxymethane and polyoxymethylene with formaldehyde being preferred. The reaction is carried out in a solvent, such as water, dioxane, methanol, or ethanol with water being preferred. In reactions were a salt of a compound of structure (1) is the starting material; an equimolar amount of a suitable base is used to neutralize the acid that forms a polyamine salt. Suitable bases include but are not limited to sodium hydroxide, potassium hydroxide, and triethylamine. The reaction is carried out at temperatures of from 0° C. to 60° C. The reaction require from 1 to 24 hours. Bis-hexahydropyrimidine derivatives of structure (2) may be isolated from the reaction zone by extraction and evaporation, as is well known in the art. Bis-hexahydropyrimidine derivatives of structure (2) may be used after isolation without further purification or may be purified by techniques well known in the art, such as chromatography and recrystallization.

In step b, a bis-hexahydropyrimidine derivative of structure (2) is contacted with an appropriate acylating agent to form a bis-acylhexahydropyrimidine of structure (3).

For example, a bis-hexahydropyrimidine derivative of structure (2) is contacted with an appropriate acylating agent. An appropriate acylating agent is one that transfers an acyl group. Appropriate acylating agents are well known in the art and include but are not limited to formic acid, acetic acid, propionic acid, formic-acetic mixed anhydride, acetic anhydride, propionic anhydride, acetyl chloride, propionyl chloride, and acetyl-O-hydroxysuccinimide. When the appropriate acylating agent is an acid the reaction is carried out in the presence of a reagent that assists in the coupling of acids and amines, such as 1,3-dicyclohexylcarbodiimide or 2-ethyl-1-ethoxycarbonyl-1,2-dihydroquinoline. When the appropriate acylating agent is an acid chloride or an acid anhydride the reaction is carried out in the presence of a base, such as triethylamine, diisopropylethylamine, or pyridine to neutralize the acid which is liberated during the course of the reaction. The reaction is carried out in a solvent, such as tetrahydrofuran, dichloromethane, ethyl acetate, acetonitrile, or dioxane. The reaction is carried out at temperatures of between 10° C. and the refluxing temperature of the solvent. Bis-acylhexahydropyrimidine derivatives of structure (3) may be isolated from the reaction zone by extraction and evaporation, as is well known in the art. Bis-acylhexahydropyrimidine derivatives of structure (3) may be used after isolation without further purification or may be purified by techniques well known in the art, such as chromatography and recrystallization.

In step c, a bis-acylhexahydropyrimidine derivatives of structure (3) is contacted with an appropriate reducing agent to form a bis-alkylhexahydropyrimidine derivatives of structure (4).

For example, a bis-acylhexahydropyrimidine derivatives of structure (3) is contacted with a molar excess of an appropriate reducing agent, such as lithium aluminum hydride, borane, or a borane complex, such as borane dimethylsulfide. The reaction is carried out in a suitable solvent. Suitable solvents for hydride reductions are well known in the art, such as toluene, diethyl ether, methyl t-butyl ether, and tetrahydrofuran (THF). The reaction is carried out at a temperatures of 10° C. to the refluxing temperature of the solvent. The bis-alkylhexahydropyrimidine derivatives of structure (4) can be isolated from the reaction zone as is well known in the art by quenching, filtration, extraction, and evaporation to give bis-alkylhexahydropyrimidine derivatives of structure (4). Bis-alkylhexahydropyrimidine derivatives of structure (4) can be used after isolation without further purification or may be purified by techniques well known in the art, such as chromatography and recrystallization.

In step d, a bis-alkylhexahydropyrimidine derivatives of structure (4) is contacted with an appropriate solvolysis agent to give a compound of structure (5) as a salt thereof.

An appropriate solvolysis agent is a protonic acid usually in the presence of a protic solvent, such as water, methanol, ethanol, water/methanol mixtures, or water/ethanol mixtures.

For example, a bis-alkylhexahydropyrimidine derivatives of structure (4) is contacted with an acid, such as hydrochloric acid, hydrobromic acid, or trifluoroacetic acid to give a compound of structure (5) as a salt. The reaction may be carried out in a solvent, such as water, methanol, ethanol, water/methanol mixtures, or water/ethanol mixtures. The selection of a suitable solvent is well known and appreciate on the art and depends on the solubility of the bis-alkylhexahydropyrimidine derivative of structure (4) and the polyamine salt of structure (5). The reaction is carried out at temperatures of from 10° C. to the refluxing temperature of the solvent. For a bis-alkylhexahydropyrimidine derivatives of structure (4) in which Y is hydrogen it is advantageous to provide for the removal of the formaldehyde which is formed during the course of the reaction, such as a sweep of an inert gas over the reaction vessel. A polyamine derivative of structure (5) can be isolated from the reaction zone as the salts thereof by precipitation and filtration. A compound of structure (5) can be purified as salts thereof by recrystallization.

Compounds of structure (5) can be isolated from their salt by methods well known in the art. Salts of the compounds of structure (5) can be exchanged as is well known in the art.

The following examples present typical syntheses as described in Scheme A. These examples are understood to be illustrative only and are not intended to limit the scope of the invention in any way. As used in the following examples, the following terms have the meanings indicated: "g" refers to grams, "mmol" refers to millimoles, "mL" refers to milliliters, "° C." refers to degrees Celsius, "$R_f$" refers to retention factor, "mp" refers to melting point, "dec" refers to decomposition, "M" refers to molar, and "TLC" refers to thin layer chromatography.

EXAMPLE 1
Step a:
1,7-Bis-(hexahydropyrimidin-1-yl)-heptane

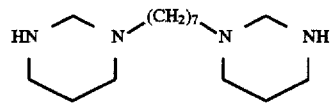

Dissolve N,N'-bis-(3-aminopropyl)-1,7-heptanediamine tetrahydrochloride salt (10.0 g, 25.6 mmol) in an aqueous 1 M sodium hydroxide solution (103 mL, 103 mmol). Cool to 5° C. in an ice-bath. Add an aqueous solution of formaldehyde (37% by weight, 3.8 mL, 50.8 mmol). Stir in the ice-bath for 1 hour and then warm to ambient temperature and stir for 1 hour. Extract the aqueous reaction mixture three times with dichloromethane (100 mL). Combine the organic layers and dry over $K_2CO_3$, filter and evaporate in vacuo to give the title compound as light yellow solid which can be used without further purification. Chromatograph on silica gel eluting with 3% concentrated aqueous ammonia solution/methanol to give an analytical sample of the title compound as a white solid: TLC $R_f$=0.46 (silica gel, 5% concentrated aqueous ammonia solution/methanol); mp; 52°–53° C. $^1$H NMR (300 MHz, $CDCl_3$) δ: 1.3 (m, 6H), 1.46, (br m, 4H), 1.61 (p, J=5.5 Hz, 4H), 1.7 (br s, 2H), 2.21 (dd, J=7.6 Hz J=8.6 Hz, 4H), 2.56 (br t, J=4.8 Hz, 4H), 2.81 (t, J=5.5 Hz, 4H), 3.37 (s, 4H). Elem. Anal. calculated for $C_{15}H_{32}N_4$: C, 67.11; H, 12.02; N, 20.87. Found: C, 66.65; H, 12.85; N, 20.69.

EXAMPLE 2
Step b:
1,7-Bis-(3-acetylhexahydropyrimidin-1-yl)-heptane

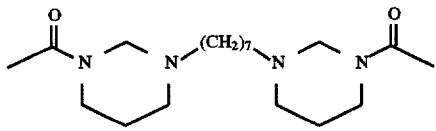

Combine 1,7-bis-(hexahydropyrimidinyl-1-yl)-heptane (5.0 g, 18.7 mmol) and triethylamine (7.6 g, 75 mmol) in ethyl acetate (40 mL). Add acetic anhydride (103 mL, 103 mmol) and heat at reflux for 8 hours. Evaporate the reaction mixture in vacuo to obtain a concentrate. Partition the concentrate between a 1M aqueous solution of sodium hydroxide (40 mL) and dichloromethane (75 mL). Extract the aqueous layer two times with dichloromethane (75 mL). Combine the organic layers and dry over $K_2CO_3$, filter, and evaporate in vacuo to give the title compound as light orange oil which can be used without further purification. Chromatograph on silica gel eluting with 10% methanol/dichloromethane to give an analytical sample of the title compound as a colorless oil: TLC $R_f$=0.35 (silica gel, 10% methanol/ dichloromethane). $^1$H NMR (300 MHz, $CDCl_3$) δ: 1.3 (m, 6H), 1.5 (m, 4H), 1.67/1.70 (overlapping, complex pentets, J=5.6/5.6 Hz 4H), 2.09/2.11 (s, 6H), 2.4 (m, 4H), 2.72/2.73 (t, J=6.3/6.3 Hz, 4H), 3.48/3.60 (t, J=5.6/5.6 Hz, 4H), 4.04/4.23 (s, 4H). Elem. Anal. calculated for $C_{19}H_{36}N_4O_2$: C, 64.74; H, 10.29; N, 15.89. Found: C, 63.13; H, 10.59; N, 15.52.

EXAMPLE 3
Step c:
1,7-Bis-(3-ethylhexahydropyrimidin-1-yl)-heptane

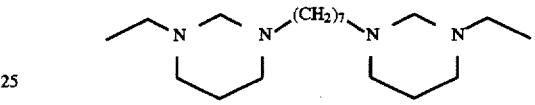

Combine lithium aluminum hydride (0.85 g, 22.7 mmol) and anhydrous tetrahydrofuran (60 mL). Add to the above suspension a solution of 1,7-bis-(3-acetylhexahydropyrimidinyl-1-yl)-heptane (2.0 g, 5.7 mmol) and anhydrous tetrahydrofuran (40 mL). Heat at reflux and stir under an inert atmosphere for 16 hours. Cool to ambient temperature. Carefully, add an saturated aqueous solution of sodium sulfate (5 mL) to quench the reaction. Stir for 16 hours to ensure a complete quench. Filter through a bed of Celite and rinse the filter cake obtained three times with tetrahydrofuran (10 mL). Evaporate the filtrate in vacuo to give a residue. Dissolve the residue in acetonitrile (50 mL) and concentrate in vacuo to give the title compound as an oil which can be used without further purification. Chromatograph on silica gel eluting with 1/20/80, concentrated aqueous ammonia solution/methanol/ dichloromethane to give an analytical sample of the title compound as a colorless oil: TLC $R_f$=0.56 (silica gel, 1/20/80, concentrated aqueous ammonia solution/methanol/ dichloromethane). $^1$H NMR (300 MHz, $CDCl_3$) δ: 1.07 (t, J=7.2 Hz, 6H), 1.3 (m, 6H), 1.46 (br m, 4H), 1.67 (p, J=5.6 Hz, 4H), 2.30 (dd, J=7.6 Hz, J=7.6 Hz, 4H), 2.39 (q, J=7.2 Hz, 4H), 2.40–2.50 (m, 8H), 3.08 (br s, 4H). Elem. Anal. calculated for $C_{19}H_{40}N_4$: C, 70.31; H, 12.42; N, 17.26. Found: C, 69.50; H, 12.75; N, 16.70.

EXAMPLE 4
Step d:
N,N'-Bis-[3-(ethylamino)propyl]-1,7-heptanediamine tetrahydrochloride

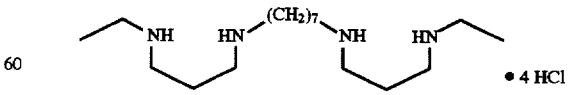

Combine 1,7-Bis-(3-ethylhexahydropyrimidinyl-1-yl)-heptane (0.50 g, 1.5 mmol) and methanol (20 mL). Add aqueous 12 M hydrochloric acid (5 mL). Heat to reflux and provide a sweep of nitrogen above the condenser to remove the formaldehyde that is released in the reaction. Periodically replace the methanol that is lost due to the nitrogen sweep. After 3 hours, cool the reaction to ambient temperature and collect the solid precipitate by filtration. Recrystallize the solid from water (0.8 mL) and 2-propanol (2.9 mL) to give the title compound as a solid; mp: 313° C. (dec); TLC $R_f$=0.39 (silica gel, 40% concentrated aqueous ammonia solution/methanol). $^1$H NMR (300 MHz, $D_2O$) δ: 1.30 (t, J=7.3 Hz, 6H), 1.40 (m, 6H), 1.70 (br p, J=7.3 Hz, 4H), 2.1 (m, 4H), 3.1 (m, 4H), 3.13 (q, J=7.3 Hz, 4H), 3.15 (m, 8H). Elem. Anal. calculated for $C_{17}H_{40}N_4$·4HCl: C, 45.74; H, 9.94; N, 12.55; Cl, 31.77. Found: C, 45.49; H, 10.48; N, 12.33, Cl, 31.20.

What is claimed is:

1. A compound of the formula

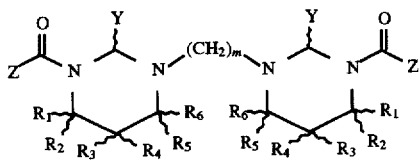

wherein m is 6, 7, 8, or 9, $R_1$, $R_2$, $R_3$, $R_4$, $R_5$, and $R_6$, are each independently hydrogen or a $C_1$–$C_3$ alkyl group with the proviso that the total number of carbon atoms incorporated by all the groups $R_1$, $R_2$, $R_3$, $R_4$, $R_5$, or R6 may not exceed 6, Z is hydrogen, methyl, or ethyl, Y is hydrogen, $C_1$–$C_6$ alkyl, phenyl, or substituted phenyl.

2. A compound according to claim 1 wherein Y is hydrogen.

3. A compound according to claim 2 wherein m is 7.

4. A compound according to claim 3 wherein Z is methyl.

5. A compound according to claim 4 wherein $R_1$, $R_2$, $R_3$, $R_4$, $R_5$, and $R_6$ are hydrogen.

6. A compound of the formula

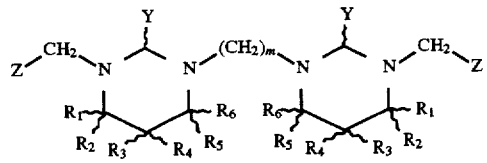

wherein m is 8 or 9, $R_1$, $R_2$, $R_3$, $R_4$, $R_5$, and $R_6$, are each independently hydrogen or a $C_1$–$C_3$ alkyl group with the proviso that the total number of carbon atoms incorporated by all the groups $R_1$, $R_2$, $R_3$, $R_4$, $R_5$, or R6 may not exceed 6, Z is hydrogen, methyl, or ethyl, Y is hydrogen, $C_1$–$C_6$ alkyl, phenyl, or substituted phenyl.

7. A compound according to claim 6 wherein Y is hydrogen.

8. A compound according to claim 7 wherein Z is methyl.

9. A compound according to claim 8 wherein $R_1$, $R_2$, $R_3$, $R_4$, $R_5$, and $R_6$ are hydrogen.

* * * * *